United States Patent [19]
Gould et al.

[11] Patent Number: 5,627,034
[45] Date of Patent: May 6, 1997

[54] ASSAY FOR CARCINOMA PROLIFERATIVE STATUS BY MEASURING NGAL EXPRESSION LEVEL

[75] Inventors: Michael N. Gould; Steven P. Stoesz, both of Madison, Wis.

[73] Assignee: Wisconsin Alumni Research Foundation, Madison, Wis.

[21] Appl. No.: 567,509

[22] Filed: Dec. 5, 1995

[51] Int. Cl.$^6$ .......................... C12Q 1/68; G01N 33/574; G01N 33/53; C07H 21/04
[52] U.S. Cl. .............. 435/6; 435/7.2; 435/7.23; 435/40.52; 536/24.31
[58] Field of Search .............. 435/7.23, 6; 536/24.3, 536/24.31, 22.1; 530/350

[56] References Cited

PUBLICATIONS

Bartsch, S. and Tschesche, H. FEBS Lett. 357:255–259 1995.

Kjeldsen, L. et al. European Journal of Clinical Investigation. 25(Suppl. 2):A33 1995.

S. Bartsch, et al., *Cloning And Expression Of Human Neutrophil Lipocalin cDNA Derived From Bone Marrow And Ovarian Cancer Cells*, 357 FEBS Letters 255–259 (1995).

J. Bundgaard, et al., *Molecular Cloning And Expression Of A cDNA Encoding NGAL: A Lipocalin Expressed In Human Neutrophils*, 202 Biochem. & Biophy. Res. Comm. 1468–1475 (1994).

L. Kjeldsen, et al., *Isolation And Primary Structure Of NGAL, A Novel Protein Associated With Human Neutrophil Galatinase*, 268 J. Bio. Chem. 10425–10432 (1993).

S. Stoesz, et al., *Isolation Of A Lipocalin Uniquely Overexpressed In Neu–Initiated Rat Mammary*, AACR Abstract (1994).

S. Stoesz, et al., *Cloning Of Genes Overexpressed In Neu–Initiated Rat Mammary Tumors*, AACR Abstract (1992).

S. Xu, et al., *The Development Of An Assay For Human Neutrophil Lipocalin (HNL)–To Be Used As A Specific Marker Of Neutrophil Activity In Vivo And Vitro*, 171 J. Immu. 245–252 (1994).

N. L. Petrakis, *Nipple Aspirate Fluid In Epidemiologic Studies Of Breast Disease*, 15 Epid. Rev. 188–195 (1993).

F. Hutchinson, et al., *Simple And Complex Cell Cycles*, 5 Animal Review 341–95 (1989).

*Primary Examiner*—Marian C. Knode
*Assistant Examiner*—John Lucas
*Attorney, Agent, or Firm*—Quarles & Brady

[57] ABSTRACT

A method of determining the proliferative status of a carcinoma is disclosed. One obtains a patient sample and then quantitatively analyzes the sample for NGAL gene expression product. The amount of NGAL expression product is compared with a standard curve to determine the S-phase value. The sample can be breast tissue or breast fluid aspirate. Alternatively, blood can by analyzed for this marker to diagnose metastasis.

11 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 197 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met Pro Leu Gly Leu Leu Trp Leu Pro Ser Leu Leu Gly Ala Leu His
 1               5                  10                  15
Ala Gln Ala Gln Asp Ser Thr Ser Asp Leu Ile Pro Ala Pro Pro Leu
            20                  25                  30
Ser Lys Val Pro Leu Gln Gln Asn Phe Gln Asp Asn Gln Phe Gln Gly
        35                  40                  45
Lys Trp Tyr Val Val Gly Leu Ala Gly Asn Ala Ile Leu Arg Glu Asp
    50                  55                  60
Lys Asp Pro Gln Lys Met Tyr Ala Thr Ile Tyr Glu Leu Lys Glu Asp
65                  70                  75                  80
Lys Ser Tyr Asn Val Thr Ser Val Leu Phe Arg Lys Lys Lys Cys Asp
                85                  90                  95
Tyr Trp Ile Arg Thr Phe Val Pro Gly Cys Gln Pro Gly Glu Phe Thr
            100                 105                 110
Leu Gly Asn Ile Lys Ser Tyr Pro Gly Leu Thr Ser Tyr Leu Val Arg
        115                 120                 125
Val Val Ser Thr Asn Tyr Asn Gln His Ala Met Val Phe Phe Lys Lys
    130                 135                 140
Val Ser Gln Asn Arg Glu Tyr Phe Lys Ile Thr Leu Tyr Gly Arg Thr
145                 150                 155                 160
Lys Glu Leu Thr Ser Glu Leu Lys Glu Asn Phe Ile Arg Phe Ser Lys
                165                 170                 175
Ser Leu Gly Leu Pro Glu Asn His Ile Val Phe Pro Val Pro Ile Asp
            180                 185                 190
Gln Cys Ile Asp Gly
        195
```

( 2 ) INFORMATION FOR SEQ ID NO:2:

( i ) SEQUENCE CHARACTERISTICS:
        ( A ) LENGTH: 660 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

```
CACGAGTCCA CCCCTGCCAG GCCCAGCAGC CACCACAGCG CCTGCTTCCT CGGCCCTGAA        60
ATCATGCCCC TAGGTCTCCT GTGGCTGCCT AGCCTGTTGG GGCTCTGCA  TGCCCAGGCC       120
CAGGACTCCA CCTCAGACCT GATCCCAGCC CCACCTCTGA GCAAGGTCCC TCTGCAGCAG       180
AACTTCCAGG ACAACCAATT CCAGGGGAAG TGGTATGTGG TAGGCCTGGC AGGGAATGCA       240
```

| | | | | | | |
|---|---|---|---|---|---|---|
| ATTCTCAGAG | AAGACAAAGA | CCCGCAAAAG | ATGTATGCCA | CCATCTATGA | GCTGAAAGAA | 300 |
| GACAAGAGCT | ACAATGTCAC | CTCCGTCCTG | TTTAGGAAAA | AGAAGTGTGA | CTACTGGATC | 360 |
| AGGACTTTTG | TTCCAGGTTG | CCAGCCCGGC | GAGTTCACGC | TGGGCAACAT | TAAGAGTTAC | 420 |
| CCTGGATTAA | CGAGTTACCT | CGTCCGAGTG | GTGAGCACCA | ACTACAACCA | GCATGCTATG | 480 |
| GTGTTCTTTA | AGAAAGTTTC | TCAAAACAGG | GAGTACTTCA | AGATCACCCT | CTACGGGAGA | 540 |
| ACCAAGGAGC | TGACTTCGGA | ACTAAAGGAG | AACTTCATCC | GCTTCTCCAA | ATCTCTGGGC | 600 |
| CTCCCTGAAA | ACCACATCGT | CTTCCCTGTC | CCAATCGACC | AGTGTATCGA | CGGCTGAGTG | 660 |

ASSAY FOR CARCINOMA PROLIFERATIVE STATUS BY MEASURING NGAL EXPRESSION LEVEL

This invention was made with United States government support awarded by NIH, Grant # CA 58328. The United States Government has certain rights in this invention.

FIELD OF THE INVENTION

This invention relates to a method for determining carcinoma proliferative status. One examines a patient sample for the level of NGAL gene expression product and uses that information to determine the relative degree of cellular proliferation.

BACKGROUND

The oncogene c-erbB-2 is known to be associated with the clinical progression of human breast cancer. In vivo models utilizing c-erbB-2's rodent homolog, neu, have been developed to try to evaluate the role of c-erbB-2 in mammary carcinogenesis and tumor biology. In one model transgenic mice have been generated in which the expression of activated neu is targeted to the mammary gland using mammary-specific promoters. In a second model the activated neu oncogene has been directly and stably introduced into in situ rat mammary epithelial cells, using a replication-defective retroviral vector. With both methods, neu was found to be a potent tumor inducer.

We previously have reported "The isolation of a lipocalin uniquely overexpressed in neu-initiated rat mammary carcinomas". S. Stoesz. et al. 1994 AACR Abstract. This lipocalin has been named "NRL" (for neu-related lipocalin). The disclosure of this abstract and of all other publications referred to herein are incorporated by reference as if fully set forth herein. As lipocalins are known to have a wide range of functions, the specific function of NRL is not known.

A protein somewhat homologous to rat NRL, human NGAL, has been isolated and sequenced. Various cDNA gene sequences coding for NGAL and NGAL's protein sequence have been reported in L. Kjeldsen, et al., *J. Biol. Chem.* 268: 10425–10432 (1993); J. Bundgaard, et al., *Biochem Biophys. Res. Comm* 202[13]: 1468–1475 (1994); S. Bartsch et al. FEBS Let. 37: 255–289 (1995). NGAL (also known as human neutrophil lipocalin/HNL) has been found in a variety of cell types (e.g. bone marrow; ovarian cell cancers). Again, its specific function is not known.

Note that Bundgaard reported the first base of the mature protein as Q from CAG, whereas Kjeldsen at one location reported an E at that position. The present claims use "NGAL" to cover both variants.

Treatment and diagnosis of breast carcinoma can be improved by a precise determination of the proliferative status of the cancer. One important measure of proliferative status is the percentage of cells in "S-phase". S-phase is the phase of the cell cycle in which duplication of DNA occurs. See generally F. Cross et al., Annu. Rev. Cell Biol. 5:341–395 (1989). Measurement of the percentage of cells in a biopsy sample that are in S-phase is an indicator of cellular proliferation status. A high percentage of cells in S-phase is known to be indicative of a poor prognosis for tumors, absent very aggressive treatment.

The percentage of carcinoma cells in S-phase has been measured by cell staining, flow cytometry, and by analyzing certain markers. Known techniques have problems (e.g. high cost; time consuming) and specific equipment requirements that make the techniques unattractive for routine clinical laboratory usage. Thus, a need exists for an improved assay to determine the proliferative status of carcinomas.

SUMMARY OF THE INVENTION

In one aspect, the invention provides a method of determining the proliferative status of a human carcinoma. One obtains a sample from a human, the sample being selected from the group consisting of a portion of the carcinoma and breast fluid. One then quantitatively analyzes the sample for NGAL gene expression product and determines the proliferative status from the quantitative analysis of the NGAL expression product.

By "quantitative" analysis we refer to analysis of the amount, or relative amount (and thus, we also intend to include semi-quantitative analysis). One proliferative status is the degree of S-phase.

In a preferred form, the method is for determining the proliferative status of a human breast tumor. NGAL RNA (e.g. mRNA), NGAL protein, or a protein having at least SEQ ID No. 1 sequences 21–197 is the expression product. The preferred sample is either a carcinoma taken from breast tissue or breast duct fluid.

The analysis can include a step where there is an immunoassay, or a step where there is probing with a nucleic acid probe complementary to the NGAL RNA. Such a probe is preferably a strand of a labelled full length cDNA of NGAL.

In another form there is provided a method for screening for the presence in a human female of a breast carcinoma. One obtains breast fluid from the female and then quantitatively analyzes the sample for marker protein associated with breast carcinomas. One then determines whether there is a breast carcinoma present in the female from the quantitative analysis of the marker protein. Preferably, the marker is the mature NGAL protein.

In another aspect, blood can be screened for elevated levels of the protein relative to normal levels (or relative to levels present in the patient when the tumor was first diagnosed). Elevated levels indicate metastasizing of the carcinoma.

It will be appreciated that one object of the present invention is to provide an assay for cancer proliferative status, particularly the percentage of S-phase.

Another object of the present invention is to provide an assay for breast cancer that does not require an invasive biopsy and can be quickly performed at relatively low cost.

Another object is to monitor breast cancer metastasis.

Other objects, features and advantages of the present invention will become apparent after examination of the specification and claims which follow.

DESCRIPTION OF THE INVENTION

OVERALL CONCEPT

The present invention provides an assay for the detection of the proliferative status of a carcinoma (especially a breast carcinoma). This assay can take the form of an assay for various "NGAL expression products" such as NGAL mRNA, NGAL protein, or NGAL protein fragments (such as the NGAL mature protein form which misses a leader sequence). An NGAL expression product quantitative reading is obtained which is compared to a standard curve (or other information data base) specifying NGAL expression product levels versus S-phase values (under the particular test). An S-phase value can thus be determined for a given patient.

A protein standard curve can be created by determining S-phase values via flow cytometry for a panel of human mammary tumor cells, then determining NGAL protein levels for those same known samples using, for example, the NGAL protein assay of S. Xu et al., J. Immunol. Meth. 171: 245-252 (1994).

An RNA standard curve can be created by comparing known S-phase values of a panel of human mammary tumor cells with the relative amount of NGAL RNA present as compared to the expression of a stably expressed RNA such as 36B4. For example, in order to normalize lane loadings, radiolabelled 36B4 cDNA, encoding acidic ribosomal phosphoprotein PO, can be used as a comparative probe. See generally Laborda, et al., Nucl. Acids Res. 19: 3998 (1991).

Using our assay we have found that NGAL expression product levels are predictive of S-phase values.

Alternatively, elevated levels of NGAL protein (or other markers) in breast fluid or blood serum can confirm carcinoma presence and/or metastasis.

OBTAINING HUMAN SAMPLES

Human female breast tissue suspected of harboring a carcinoma can be obtained by standard biopsy methods known to one of skill in the art. For example, aspiration (or fine needle) biopsy, which involves the aspiration of cells and tissue fragments through a needle that has been guided into the suspect tissue, may be used. Needle (or core) biopsy, which involves obtaining a core of tissue through a specially designed needle introduced into the suspect tissue, is another option.

Incisional biopsies, which involve the removal of a small wedge of tissue from a larger tumor mass, and excisional biopsies, which involve an excision of the entire suspected tumor tissue with little or no margin of surrounding normal tissue, are other examples of suitable tissue extraction methods. See generally V. DeVita, Jr., et al., *Cancer Principles and Practice of Oncology* Vol. 1, 4th Ed. J. B. Lippincott Co., pp. 243-244 (1993).

The tissue may be prepared as follows for RNA analysis. Tissues are rapidly frozen in liquid nitrogen. Following storage at −80° C. the tissues are ground into fine powder and homogenized. Total RNA can be isolated using the acid guanidinium thiocyanate-phenol-chloroform extraction method of P. Chomcynski et al., 162: 156-159 Anal. Biochem. (1987).

Tissue may instead be prepared as follows for protein analysis. In order to extract protein, tissue can be homogenized with a Polytron in PBSTDS (10 mM sodium phosphate, dibasic; 154 mM sodium chloride; 12 mM deoxycholic acid, sodium salt; 1 mM sodium fluoride; 3.5 mM sodium dodecyl sulfate (SDS); 31 mM sodium azide; 1% Triton X-100; 1 mM phenylmethylsulfonyl fluoride) at a concentration of 100 mg per ml, and centrifuged at 10,000 g for 15 min at 4° C. One then removes the supernatant containing the soluble protein.

An alternative preferred sample is breast duct fluid, preferably a nipple fluid aspirate. NGAL protein contains a leader sequence which is believed to facilitate the delivery of the NGAL protein and protein fragments into the lumen of the breast duct system. Thus, one protocol is to measure such protein markers in breast fluid aspirate. No biopsy is required.

Nipple aspirate fluid can be obtained using a modified breast pump. See N. Petrakis, *Epidemiologic Reviews*, 15(1):188-195 (1993). Such pumps consist of a 10 or 15 ml syringe attached by means of a short plastic tube to a small cup that fits over the nipple. The patient gently, but firmly, compresses the breast with both hands, and the plunger of the syringe is withdrawn to the 10 ml level and held until fluid appears at the surface of the nipple. The fluid is collected with nonheparinized capillary tubes and used for cytologic and biochemical studies.

ASSAYS

A. RNA

We describe below a Northern blot procedure. Other general RNA measurement techniques are known to one of skill in the art and could be used instead. Northern blot analysis involves isolation of total RNA from the tissue samples. The RNA is then electrophoresed on an electrophoretic gel, preferably an agarose gel, and blotted onto a membrane. The membranes are then washed and probed with radioactive nucleotide probes that are homologus to a segment of the RNA. Hybridization between labelled DNA probe and the target RNA can be visualized by autoradiography or PhosphorImager screening.

One Northern blot probe is the full SEQ ID NO:2 sequence, which is a cDNA sequence of the human NGAL gene. SEQ ID NO:1 is NGAL itself.

One then compares the intensity of the RNA from NGAL to that from 36B4, and then compares that normalized reading to normalized readings in a standard curve to find the S-phase percentage. The S-phase measurement indicates the percentage of cells that are in the DNA duplication stage. The higher the percentage, the greater the concern. Some have reported that levels above 6.4% are of serious concern for disease free survival, and others have reported that levels above 10% are of very serious concern for disease free survival.

In interpreting these results, doctors may want to keep in mind that there are indications from rat experiments that females in involution are likely to have slightly elevated levels of marker protein. Thus, a positive at that time should be double checked.

B. Protein In A Solid Sample

Alternatively, one may examine patient tissue from a mammary carcinoma for the absolute amount of the NGAL protein. This examination can be done via an RIA. See e.g. S. Xu. et al., J. Immunol. Meth. 171: 245-252 (1994). It can also be done via an enzyme-linked immunosorbent assay (ELISA) reaction. In an ELISA, one would expose the sample to an antibody specific for NGAL. Polyclonal antiserum to NGAL can be obtained from a rabbit that has been immunized with NGAL. After binding of the polyclonal antibody to NGAL protein, one exposes the mixture to a second antibody (e.g. goat anti-rabbit) that is linked to an enzyme color change label. Detection of this label indicates the presence of NGAL antigen.

More specifically, anti-NGAL (monoclonal or polyclonal) capture antibodies can be coated on microtiter plates. Following washes, patient samples containing unknown NGAL antigen concentration levels are incubated on the plates. After washing out unbound antigen, a secondary anti-NGAL antibody is added to the wells and incubated. This secondary antibody may be enzyme-labelled, or is followed with a tertiary enzyme-labelled antibody which recognizes the secondary, but not capture, antibodies. After unbound antibody is washed out, an appropriate chromogenic enzyme substrate is added to the wells. The degree of color change produced with the substrate's incubation is proportional to the concentration of NGAL derived protein in the tumor sample, and is compared to known concentration standards of recombinant NGAL run in parallel. See E. Engvall, et al., *Immunochemistry* 8: 871–879 (1971) for general ELISA techniques.

From an examination of the ELISA results, one would be able to determine the level of NGAL protein present in patient tissue samples and compare this to a tumor panel with known prognostic and S-phase histories. One could also use other methods, such as Western blots, to analyze the amount of NGAL protein in a sample.

C. Protein In Breast Fluid

If one wishes to examine mammary duct fluid or blood, one would assay directly for NGAL protein (or protein fragment) through the above assays. If desired, the total protein of the sample liquid may first be isolated by known techniques, with the assay then being conducted on the total protein. One may also wish to examine mammary duct aspirate (or other samples such as blood) for the presence of other proliferation markers besides just NGAL protein to supplement the diagnosis.

KNOWN HUMAN BREAST TUMOR SAMPLES

We examined tissue RNA from 15 random human breast tumors with known S-phase percentages (the S-phase percentages were reported to us by others). We found by Northern blot analysis that four samples indicated the presence of high levels of NGAL RNA. The results are tabulated below in Table 2.

TABLE 2

| TUMOR | NGAL | S-PHASE (%) |
|---|---|---|
| 1 | − | 3.2 |
| 2 | − | 3.1 |
| 3 | − | 3.7 |
| 4 | − | 1.1 |
| 5 | ++ | 22.3 |
| 6 | − | 1.6 |
| 7 | − | 10.4 |
| 8 | − | 9.0 |
| 9 | ++ | 15.3 |
| 10 | + | 4.0 |
| 11 | − | 1.5 |
| 12 | + | 14.6 |
| 13 | − | 8.2 |
| 14 | − | 1.6 |
| 15 | − | 5.5 |

A symbol of + or ++ indicates that expressed, or strongly expressed, respectively, NGAL RNA was detected on the Northern blot. Statistical analysis shows the S-phase association with NGAL to be p = 0.0051.

RAT EXPERIMENTS

The activated neu (HER2/c-erbB-2) oncogene is extremely potent in inducing mammary cancer. For example, neu induces greater than 200 times as many tumors as the activated ras oncogene when directly introduced into in situ rat mammary epithelial cells using replication-defective retroviral vectors. In order to characterize mechanisms underlying this potency, we identified uniquely overexpressed genes in neu-initiated rat tumors that were not overexpressed in tumors induced by weaker initiating agents.

One rat gene, encoding a member of the lipocalin and calycin protein families, was 12-fold overexpressed in neu mammary tumors and was not overexpressed in ras or chemically induced carcinomas. This uniquely overexpressed gene has been termed neu-related lipocalin (NRL). The NRL protein was produced in quantity in a baculovirus system, purified, and used to generate polyclonal antibodies. Western blot analysis indicated that neu-initiated mammary carcinomas express abundant NRL protein when compared to other mammary tumors. The entire cDNA sequence of NRL was determined and analyzed for homology to known databased genes.

The cDNA sequence of human NGAL (SEQ ID NO:2) is about 72% homologous to NRL cDNA. However, while activation of neu overexpresses NRL in rats, activation of c-erbB-2 in humans does not lead to overexpression of NGAL.

a. Recombinant NRL Protein Production cDNA of NRL was used to produce recombinant NRL protein in a baculovirus system. Cotransfection and viral amplification led to a modest concentration of secreted protein from *Spodoptera frugiperda* (sf9) insect cells. In contrast, greatly enhanced secreted lipocalin production, approximately 25 μg per ml of serum-free media, was generated by infection of *Trichoplusia ni* (Tni) insect cells. Approximately 3.5 mg of protein was purified and concentrated to 170–270 μg per ml using high pressure liquid chromatography (HPLC). Polyclonal antibodies were generated in two rabbits using the HPLC-purified and concentrated NRL product.

Pathogen-free virgin female WF [Wistar Furth] rats were purchased from Harlan Sprague-Dawley, Inc. (Madison, Wis.), given food and acidified water ad libitum, and housed under a 12-hour light, 12-hour dark cycle. Mammary tumors initiated by the introduction in situ of activated neu and v-Ha-ras were produced, as were mammary tumors induced by the carcinogens DMBA [dimethylbenz(a)anthracene] and NMU [N-nitroso-N-methylurea].

b. Total and Messenger RNA Isolation

Normal tissue and mammary carcinomas were removed from rats and rapidly frozen in liquid nitrogen. Following storage at −80° C. the tissues were ground into fine powder and homogenized. Total RNA was isolated. The purity and integrity of the harvested RNA was monitored by its 260/280 absorbance ratio and electrophoresis in denaturing formaldehyde-agarose. Poly(A)$^+$ RNA suitable for in vitro translation, cDNA synthesis and radiolabeled probes was isolated using the PolyATtract mRNA isolation system (Promega, Madison, Wis).

c. In Vitro Translation and Two-Dimensional Gel Analysis

One μg of poly(A)$^+$ RNA was translated in vitro using the following reaction conditions: 35 μl nuclease-treated rabbit reticulocyte lysate (Promega), 1 μl 1 mM amino acid mixture (minus methionine), 4 μl [$^{35}$S]—methionine (DuPont NEN, Boston, Mass; 1200 Ci/mmol, 10 mCi/ml), and H$_2$O to 50 μl. The translation reactions were carried out at 30° C. for 60 minutes, and their efficiencies determined by trichloroacetic acid protein precipitation.

Approximately 250,000 cpm of translated product was analyzed by two-dimensional electrophoresis. Following electrophoresis, gels were fixed in 50% methanol and 10% acetic acid overnight, treated with EnHance (DuPont NEN) for 1 hour, rehydrated in water for 30 minutes, dried onto filter paper and autoradiographed.

d. cDNA Library Synthesis

A cDNA library representing a neu tumor's mRNA population was produced using the SuperScript plasmid system (Life Technologies, Gaithersburg, Md.). Three μg of template poly(A)$^+$ RNA was derived from a monoclonal neu-initiated mammary carcinoma resected 8 weeks after retroviral infusion. Complementary DNA representing this mRNA was directionally cloned into the NotI and SalI sites of the pSport 1 vector provided with the system. Introduction of the ligated recombinant vector into Max Efficiency DH5α competent cells (Life Technologies) produced a representative library of $3.9 \times 10^5$ clones. A glycerol stock of the library was stored at −80° C.

e. Differential Screening

The neu-initiated tumor cDNA library was plated at a density of approximately 2000 colonies per 90 mm LB/ampicillin plate. Two replicate lifts were grown using Nytran transfer and immobilization membranes (Schleicher and Schuell, Keene, NH). DNA was immobilized on membranes according to their manufacturer's specifications. Poly $(A)^+$ RNAs from neu tumor and normal mammary tissue were reverse transcribed into first strand cDNAs with Moloney murine leukemia virus reverse transcriptase (Life Technologies), generating probes radiolabeled with $[\alpha\text{-}^{32}P]\text{-dCTP}$ (DuPont NEN). RNA template was then hydrolyzed with 0.3N NaOH at 68° C. for 20 minutes, and the remaining probe neutralized and purified with two 2.5M $NH_4OAc$/ethanol precipitations. The replicate membranes underwent prehybridization, hybridization and washing according to their manufacturer's instructions, with probe concentrations of $1 \times 10^6$ cpm/ml. Autoradiographs of these differential screens revealed candidate colonies which hybridized more strongly to tumor than normal probes. These clones were picked, streaked, and subjected to two additional rounds of differential screening, to both colony purify and verify their differential expression. Plasmids from positive colonies were grown in LB media with ampicillin and harvested using alkaline lysis and Qiagen-tip 100 anion exchange columns (Qiagen, Chatsworth, Calif.). The cDNA inserts were excised from vector DNA with MluI (New England Biolabs, Beverly, Mass.) and purified with preparative 1% agarose gels (SeaKem GTG, FMC, Rockland, Me.).

f. Northern Blot Analysis

Eight μg of total RNA from mammary tumors and various tissues were separated on 1% denaturing formaldehyde-agarose gels, and transferred to GeneScreenPlus nylon membranes (DuPont NEN) by pressure blotting (PosiBlot, Stratagene, La Jolla, Calif.) for 2–4 hours with 10×SSC. Following RNA transfer, membranes were baked at 80° C. for 2 hours. Candidate cDNA inserts were radiolabeled using random primers (Prime-a-Gene system, Promega), purified on Sephadex G-50 columns (Pharmacia Biotech, Uppsala, Sweden) and used as probes at concentrations of $5 \times 10^5$ cpm/ml. Prehybridization, hybridization, and washing of the membranes were accomplished following their manufacturer's specifications. Washed membranes were subjected to autoradiography for visualization, or exposed to PhosphorImager screens (Molecular Dynamics, Sunnyvale, Calif.) for quantitative analysis.

g. Protein Production and Isolation

Recombinant protein was expressed in insect cells using a baculovirus system. Full length isolated cDNA was directionally inserted into the XmaI and NotI sites of baculovirus transfer vector pVL1393, placing the gene under the transcriptional control of the polyhedrin locus. Cotransfection was accomplished with BaculoGold DNA (Pharmingen, San Diego, Calif.), a lethally modified *Autographa californica* nuclear polyhedrosis virus (AcNPV) genome. Virus amplification and titer assays were performed with *Spodoptera frugiperda* (Sf9) cells (Pharmingen). Secreted protein produced in serum-free insect cell medium Ex-Cell 400 (JRH Biosciences, Lenexa, Kans.) was collected 3 days following infection of Trichoplusia ni (Tni) cells (Invitrogen, San Diego, Calif.), with multiplicities of infection (moi) between 3 and 5. Protein was purified and concentrated by ion exchange on a 1.6×14 cm SP Sepharose fast flow column (Pharmacia Biotech), eluting with a 0 to 1.0M NaCl gradient in 20 mM 2-[N-Morpholino]ethanesulfonic acid (MES), pH 6. Protein quantitation was performed by Bradford protein assay (Bio-Rad, Richmond, Calif.) and spectrophotometry. Column fractions were stored at −20° C.

h. Polyclonal Antibody Generation

Two female New Zealand white rabbits (New Franken, New Franken, Wis.) were initially immunized with 100 μg purified recombinant protein. The protein was diluted in Dulbecco's phosphate-buffered saline (D-PBS) (Life Technologies) and emulsified with a Polytron homogenizer (Brinkmann, Westbury, N.Y.) in an equal volume of complete Freund's adjuvant (Sigma, St. Louis, Mo.). The mixture was administered intradermally in 10–20 sites. In two 4 week increments, booster injections were given subcutaneously, using 50 μg diluted protein and incomplete Freund's adjuvant (Sigma), emulsified as above. Thirty ml whole blood was collected 10 days following boosts, clotted and centrifuged at 3000 g for 15 min at 4° C., and antiserum frozen at −80° C. Relative antibody production, specificity and background were determined by indirect enzyme-linked immunosorbent assay (ELISA) (Pierce, Rockford, Ill.), using bovine serum albumin and preimmune rabbit serum as negative controls.

i. Western Blot Analysis

In order to extract protein, tumors and tissue were homogenized with a Polytron in PBSTDS (10 mM sodium phosphate, dibasic; 154 mM sodium chloride; 12 mM deoxycholic acid, sodium salt; 1 mM sodium fluoride; 3.5 mM sodium dodecyl sulfate (SDS); 31 mM sodium azide; 1% Triton X-100; 1 mM phenylmethylsulfonyl fluoride) at a concentration of 100 mg per ml, and centrifuged at 10,000 g for 15 minutes at 4° C. The soluble protein concentration was measured using the Lowry method (Peterson, *Anal. Biochem.* 83: 346–356, 1977), and 20 Rg of each sample were reduced with-mercaptoethanol and run on 10% SDS-PAGE with 25 mM Tris, 187 mM glycine and 0.1% SDS running buffer. Proteins were transblotted onto a PVDF [polyvinylidene difluoride] membrane (Immobilon, Millipore, Bedford, Mass.) overnight at 30 mA and approximately 130 volts using 25 mM Tris, 192 mM glycine and 20% methanol as transfer buffer. Membranes were blocked with 5% nonfat dry milk (NFDM), 20% calf serum in D-PBS with 0.1% Tween 20. Primary rabbit antiserum was added at a 1/10000 concentration and incubated for 2 hours. Following three 5 minute washes in D-PBS with 0.1% Tween 20, a goat anti-rabbit IgG secondary antibody conjugated to horseradish peroxidase (Life Technologies) was added at a 1/5000 concentration in blocking buffer. After a 1 hour incubation, the membrane was again washed three times, and developed with DAB [3,3'-Diaminobenzidine] peroxidase substrate (Sigma) for approximately one minute. The reaction was stopped in water, the membrane dried, and photographed. Quantitation of bands was accomplished with a ScanJet Plus desk scanner (Hewlett Packard, Palo Alto, Calif.) and the computer program Collage 2.0 (Fotodyne, New Berlin, Wis.).

UTILITY

The present invention is believed to be useful for medical screening and as a diagnostic tool. It will be appreciated that the above preferred embodiments are merely examples of the invention. Many other variations are believed to be within the scope of the claims. Thus, the claims should be looked to in order to judge the full scope of the invention.

We claim:

1. A method of determining the relative degree of proliferation of a human breast carcinoma, comprising:
   (a) obtaining a sample of carcinoma from human breast tissue;
   (b) quantitatively analyzing the sample for an NGAL gene expression product; and
   (c) determining the relative degree of proliferation of the carcinoma from the quantitative analysis of the NGAL expression product by determining whether NGAL protein is present in a concentration above a selected normal human value.

2. The method of claim 1, wherein NGAL RNA is the expression product.

3. The method of claim 1, wherein NGAL protein is the expression product.

4. The method of claim 1, wherein a protein having at least SEQ ID No. 1 sequences 21–197 is the expression product.

5. The method of claim 1, wherein the analysis includes a step comprising an immunoassay.

6. The method of claim 2, wherein the analysis includes a step comprising hybridization with a nucleic acid probe complementary to the RNA.

7. The method of claim 3, wherein the analysis includes a step where there is use of an antibody that has specificity for NGAL protein.

8. A method for screening for the presence in a human female of a breast carcinoma, comprising:
   (a) obtaining a sample of breast fluid from the female;
   (b) quantitatively analyzing the sample for NGAL protein; and
   (c) determining from the analysis whether further testing for the presence of a breast carcinoma is warranted by determining whether NGAL protein is present in a concentration above a selected normal human value.

9. The method of claim 8, where in the marker protein comprises SEQ ID NO.:1 sequences 21–197.

10. A method for screening for the presence in a human female of a metastasizing breast carcinoma, comprising:
    (a) obtaining a blood sample from the female;
    (b) quantitatively analyzing the sample for NGAL protein associated with breast carcinomas; and
    (c) determining from the analysis whether further testing for the presence of a metastasizing breast carcinoma is warranted by determining whether NGAL protein is present in a concentration above a selected normal human value.

11. The method of claim 10, where in the marker protein comprises SEQ ID NO.:1 sequences 21–197.

* * * * *